United States Patent
Plumptre et al.

(10) Patent No.: US 10,449,301 B2
(45) Date of Patent: Oct. 22, 2019

(54) ASSEMBLY FOR A DRUG DELIVERY DEVICE COMPRISING A FEEDBACK FEATURE

(71) Applicant: SANOFI-AVENTIS DEUTSCHLAND GMBH, Frankfurt am Main (DE)

(72) Inventors: David Aubrey Plumptre, Worcestershire (GB); Naceur Rekaya, Warwickshire (GB); Paul Richard Draper, Worcestershire (GB); Paul Griffin, Worcestershire (GB); Stephen Francis Gilmore, Bristol (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 717 days.

(21) Appl. No.: 14/770,845

(22) PCT Filed: Mar. 10, 2014

(86) PCT No.: PCT/EP2014/054528
§ 371 (c)(1),
(2) Date: Aug. 27, 2015

(87) PCT Pub. No.: WO2014/139916
PCT Pub. Date: Sep. 18, 2014

(65) Prior Publication Data
US 2016/0008549 A1 Jan. 14, 2016

(30) Foreign Application Priority Data
Mar. 13, 2013 (EP) ..................... 13159050

(51) Int. Cl.
*A61M 5/315* (2006.01)
*A61M 5/50* (2006.01)

(52) U.S. Cl.
CPC ...... *A61M 5/3157* (2013.01); *A61M 5/31541* (2013.01); *A61M 5/31551* (2013.01);
(Continued)

(58) Field of Classification Search
CPC .......... A61M 5/31541; A61M 5/31551; A61M 5/3157; A61M 5/31585; A61M 5/5086; A61M 2205/581
See application file for complete search history.

(56) References Cited

U.S. PATENT DOCUMENTS 5,391,157 A * 2/1995 Harris ............... A61M 5/31511
604/208
6,620,133 B1 9/2003 Steck
2010/0268171 A1 10/2010 Moller

FOREIGN PATENT DOCUMENTS

CN 1089510 7/1994
CN 101072595 11/2007
(Continued)

OTHER PUBLICATIONS

International Search Report for Int. App. No. PCT/EP2014/054528, completed May 12, 2014.
(Continued)

*Primary Examiner* — Theodore J Stigell
(74) *Attorney, Agent, or Firm* — Fish & Richardson P.C.

(57) ABSTRACT

An assembly for a drug delivery device is provided, the assembly comprising an actuator which is configured to be operated in order to dispense a dose of medication and a feedback feature being configured to give a feedback signal to a user at the end of a dwell period after the actuator has reached an end position.

20 Claims, 14 Drawing Sheets

(52) U.S. Cl.
CPC ...... *A61M 5/31585* (2013.01); *A61M 5/5086* (2013.01); *A61M 2205/581* (2013.01); *A61M 2205/582* (2013.01); *A61M 2205/583* (2013.01)

(56) References Cited

FOREIGN PATENT DOCUMENTS

| EP | 0594357 | 4/1994 |
|----|---------|--------|
| JP | 2001-517496 A | 10/2001 |
| JP | 2007-517613 A | 7/2007 |
| WO | 02/092153 | 11/2002 |
| WO | 2005/018721 | 3/2005 |
| WO | 2005/70485 A1 | 8/2005 |
| WO | WO 2006/062788 | 6/2006 |
| WO | 2006/114396 | 11/2006 |
| WO | 2012/025639 A1 | 3/2012 |

OTHER PUBLICATIONS

Japanese Office Action for JP App. No. 2015-562058, dated Dec. 18, 2017.
International Preliminary Report on Patentability and Written Opinion in Application No. PCT/EP2014/054528, dated Sep. 15, 2015, 6 pages.

\* cited by examiner

ASSEMBLY FOR A DRUG DELIVERY DEVICE COMPRISING A FEEDBACK FEATURE

CROSS REFERENCE TO RELATED APPLICATIONS

The present application is a U.S. National Phase Application pursuant to 35 U.S.C. § 371 of International Application No. PCT/EP2014/054528 filed Mar. 10, 2014, which claims priority to European Patent Application No. 13159050.7 filed Mar. 13, 2013. The entire disclosure contents of these applications are herewith incorporated by reference into the present application.

TECHNICAL FIELD

The present disclosure relates to an assembly for a drug delivery device. The assembly comprises a feedback feature.

SUMMARY

It is an object of the present invention to provide an assembly for a drug delivery device having improved properties.

According to one embodiment, an assembly for a drug delivery device is provided. The assembly comprises an actuator which is configured to be operated in order to dispense a dose of medication. The assembly further comprises a feedback feature being configured to give a feedback signal to a user at the end of the dwell period after the actuator has reached an end position. In particular, the dwell period starts when the actuator has reached an end position. The dwell period may be the time between the moment when the actuator has reached its end position and the moment when the full amount of a dose has been dispensed. In particular, the feedback signal may indicate to a user that the actuator may be released and the device may be withdrawn from a user's skin.

The advantage of a feedback feature being configured to indicate the end of a dwell period is that a clear indication is given to a user when a full amount of a dose of medication has been dispensed. Thereby, the use of the drug delivery device may be simplified for a user. Furthermore, the dosing accuracy of a drug delivery device may be increased. In particular, it may be inhibited that a user interrupts a dispense operation, for example by withdrawing the drug delivery device from the skin, before a complete dose has been delivered. Furthermore, such a feedback provides an additional benefit for visually impaired users.

The feedback signal may be an audible and/or tactile and/or visible feedback, for example. The audible feedback may be, for example, an audible click. The tactile feedback may be, for example, an impact on the skin of a user, in particular on a user's finger. For example, the tactile feedback may be a vibration of a part of the assembly. In particular, the feedback may be a well-defined signal.

The end position of the actuator may be a most distal position of the actuator. The term "most distal position" may describe a position of a part of the assembly which is closest to a dispensing end of the drug delivery device. In particular, the actuator may be in its end position when it is fully depressed into the drug delivery device. The actuator may be configured as a button.

According to one embodiment, the assembly comprises a piston. The piston may be configured to be moved in a cartridge towards a distal end of the device, in order to deliver a medication. The piston may be moved by a piston rod. The piston may comprise an elastic material. Thereby, the piston may be configured to be compressed during a dispense operation. In particular, the piston may be compressed due to a force being exerted on the piston by the piston rod and due to a pressure of a fluid in the medicament cartridge When the piston rod is not further moved towards a dispensing end of the device, in particular when the actuator has reached its end position, the piston may relax to its uncompressed form. In particular, the piston may expand in a direction towards the dispensing end of the device. Thereby, a medication may be delivered from the device, in particular after the actuator has reached its end position. Preferably, the feedback signal occurs after a relaxation of the piston to its uncompressed form. In particular, the end of the dwell period may be accomplished when the piston has relaxed to its uncompressed form.

According to one embodiment, the feedback feature comprises a snap feature. The snap feature is configured to snap through when it is compressed above a certain load. Thereby, a feedback may be given to a user. In particular, the snap feature is configured to snap through at the end of a dwell period. Initially during compression of the snap feature, the stiffness of the snap feature may remain fairly constant. At a certain point, the stiffness of the snap feature may reduce significantly. Thereby, the force required to cause a further deflection of the snap feature may decrease. This may cause the snap-through behaviour of the snap feature.

According to one embodiment, the snap feature may be configured to be compressed between two parts of the assembly. For example, the feedback feature may be compressed between a body part and a further part of the assembly which is axially moveable with respect to the body part.

According to one embodiment, the snap feature may comprise the shape of a dome. In particular, the snap feature may be configured as a snap dome. In particular, the snap feature may comprise the shape of an arched disk. According to one embodiment, the snap feature comprises a metal material. According to a further embodiment, the snap feature may comprise a plastic material. Preferably, the feedback feature comprises a resilient material.

According to one embodiment, the snap feature comprises at least one recess. The recess may be, for example, a concave cut out. Due to the at least one recess, the snap feature may comprise a sufficient flexibility. Thereby, the snap feature may be configured to snap through when it is compressed above a certain load. In particular, the size and shape of the recess may influence the force which is necessary to cause the snap feature to snap through.

According to one embodiment, the feedback feature comprises an opening, wherein at least one element of the assembly extends through the opening. For example, the piston may extend through the opening of the feedback feature.

According to one embodiment, the feedback feature is configured to axially move during the dwell period. In particular, the feedback feature may be moved between two stops. The stops may be provided by a body part. In particular, the feedback feature may interact with the stops. In particular, the feedback feature may be configured to snap through, when it abuts one of the stops. Thereby, a feedback may be created. In particular, a first feedback signal may be created at the beginning of the dwell period, when the feedback feature abuts a first stop. A second feedback signal may be created at the end of the dwell period, when the feedback feature abuts the second stop.

According to one embodiment, the feedback feature comprises a first feedback element and a second feedback element. The first feedback element may be configured to interact with the second feedback element. In particular, the first feedback element and the second feedback element may abut each other, in particular at the end of a dwell period. In particular, the second feedback element may exert a force on the first feedback element after the actuator has reached its end position. Thereby, the first feedback element may be deflected by the second feedback element during or at the end of the dwell period. The first feedback element may be, for example, a resilient element. The second feedback element may be, for example, a rigid element. For example, the second feedback element may be a protrusion in a part of the assembly. In particular, the second feedback element may extend along the whole circumference of the part. For example, the second feedback element may be a protrusion which extends along an inner circumference of a body part of the assembly. When the first feedback element and the second feedback element interact with each other, an audible feedback may be created. The first feedback element may be an integral part of a part of the device.

According to one embodiment, the feedback feature comprises at least one flexible arm.

In particular, the first feedback element may comprise at least one flexible arm. Preferably, the feedback feature comprises two or more flexible arms. Preferably, at least one flexible arm extends in a distal direction. The distal direction may be a direction towards the dispensing end of the device. In an alternative embodiment, the at least one flexible arm extends in a proximal direction. The proximal direction may be a direction away from the dispensing end of the device. According to one embodiment, the at least one flexible arm may stick out from an element of the assembly in a radial direction. During or at the end of the dwell period, the at least one flexible arm may be deflected, in particular in a radial direction. According to a further embodiment, the flexible arm may be deflected in a tangential direction with respect to a part of the assembly. Preferably, the at least one flexible arm is integrally formed with a part of the assembly. Preferably, the at least one flexible arm is attached to, in particular integrally moulded with an injection moulded part of the device.

According to one embodiment, the assembly comprises a resilient member, wherein the resilient member is deformed during the setting or the dispensing of a dose. A feedback signal may occur after a relaxation of the resilient member. The resilient member may start to relax when the actuator has reached its end position. In particular, the relaxation of the resilient member may cause the feedback signal. According to a preferred embodiment, the time which the resilient member needs to relax determines the dwell period.

The resilient member may be a spring member, for example a coil spring or a torsion spring. A relaxation of the resilient member may cause a movement of a further member of the assembly. The member may be configured to interact with the feedback feature. For example, the relaxation of the resilient member may cause a movement of a driver. The driver may be a part of the assembly which is configured to drive a piston rod in order to dispense a dose of medication. In particular, the driver may be engaged with the piston rod. During a dispense operation, the driver may be moved towards a distal end of the device due to a movement of the actuator. Due to the movement of the driver which may be caused by the relaxation of the resilient member, a medication may be delivered from the device after the actuator has reached its end position. When the further member, in particular the driver, has reached an end position after a relaxation of the resilient member, the full amount of a dose has been delivered and a feedback signal occurs.

According to one embodiment, the resilient member may be a part of the feedback feature. In particular, a feedback signal may be given by the resilient member. For example, the resilient member may create a feedback when it relaxes to its undeformed shape. For example, the resilient member may be configured to snap through, thereby creating a feedback signal. The resilient member may be a snap feature, for example a snap dome.

According to one embodiment, the assembly may comprise a member which is configured to interact with the feedback feature in order to cause a signal at the end of the dwell period. In particular, the member may be configured to compress the feedback feature. The member may be configured to axially move during the dwell period, for example rotate and axially move. In particular, the member may move after the actuator has reached its end position. A movement of the member may be caused by a relaxation of the resilient member.

According to one embodiment, the assembly may comprise a ratchet feature. The resilient member, in particular a spring member, may be coupled to the ratchet feature. The spring member may be a torsion spring. The ratchet feature may comprise a plurality of steps or teeth. In particular, the resilient member may comprise a free end which may be arranged between two steps or teeth of the ratchet feature, at least when the device is not operated. The ratchet feature may be arranged circumferentially around an outer circumference of a part of the drug delivery device. For example, the ratchet feature may be arranged at a member which is rotationally fixed during the setting of a dose and rotationally moveable during the dispensing of a dose. In particular, the member may be disengaged from a body part of the device when the actuator has reached its end position. The resilient member, in particular the spring member, may be wound around the member. In particular, the spring member may be arranged concentrically with respect to the ratchet feature.

According to one embodiment, the resilient member may be decoupled from the ratchet feature when a load on the resilient member exceeds a certain value. In particular, the resilient member may be temporarily decoupled from the ratchet feature when a deformation of the resilient member during the setting of a dose exceeds a certain value. Thereby, the load on the resilient member may not exceed a certain value throughout the setting of a dose.

According to one embodiment, the assembly may comprise a clutch member which is coupled to the ratchet feature. Furthermore, the clutch member may be coupled to the resilient member. The clutch member may be decoupled, in particular temporarily disengaged from the ratchet feature when the load on the resilient member exceeds a certain value. In particular, when a load on the resilient member exceeds a certain value, the clutch member may be rotated by the resilient member. Thereby, the clutch member may rotate with respect to the ratchet feature. In particular, the clutch member may rotate with respect to the ratchet feature when a load on the resilient member is greater than a retention force between the clutch member and the ratchet member.

According to one embodiment, the assembly may comprise a first feedback element which is configured to rotate with respect to a second feedback element. The feedback element may comprise a flexible arm. The second feedback element may comprise spline features which may be arranged at a body part of the assembly, in particular around an inner circumference of the body part. In particular, the first feedback element may be configured to interact with the spline features in order to give a feedback at the end of the dwell period.

According to one embodiment, the assembly may comprise a damping feature, wherein the damping feature retards a relaxation of the resilient member. In particular, the damping feature may be configured to retard the movement of a member which is moved, in particular rotated by the resilient member. The damping feature may comprise a viscous fluid which is arranged between two parts of the assembly. Due to the viscous fluid, a sheer stress may be generated during a movement of one of the two parts.

According to one embodiment, the assembly may comprise the piston rod, wherein the feedback feature is arranged at a distal end of the piston rod. As an example, the assembly may comprise an element which is arranged at a distal end of the piston rod. In particular, the piston rod may be partially arranged inside the element. The feedback feature may be arranged inside the element. The element may be in contact with the piston. During a dispense operation, the feedback feature may be compressed by the piston rod. When the actuator has reached its end position, the feedback feature may deflect to its uncompressed shape. Thereby, the feedback feature may expand in an axial direction. Thereby, the feedback feature may move the element, respectively the piston further towards a dispensing end of the device. At a certain point, the feedback feature may snap back into its uncompressed form. Thereby, a feedback signal may be created. In particular, the feedback feature may snap back at the end of the dwell period. In an alternative embodiment, the feedback feature may be located anywhere in the load path between the actuator and the piston.

According to a further embodiment, the assembly may comprise an electronic module which is configured to track the motion of components of the assembly in order to determine when the actuator is in an end position. Preferably, the electronic module gives the feedback signal at the end of the dwell period. In particular, when the actuator is in its end position, a countdown may start which indicates the dwell period to a user. At the end of the dwell period, the electronic module may create an audible sound or a tactile feedback, for example a vibration, or a visible feedback, for example a blinking of a display.

Furthermore, a drug delivery device is provided, the drug delivery device comprising an assembly which is configured as previously described. In particular, the drug delivery device may comprise a feedback feature, which is configured to indicate an end of a dwell period to a user by giving an audible and/or tactile and/or visible feedback.

The drug delivery device may be an injection device. The drug delivery device may be a pen-type device. The drug delivery device may be a variable dose device such that a user can select the size of a dose. The drug delivery device may be configured for multiple dose applications. The medication may be delivered to a user by means of a needle. The device may be delivered to a user in a fully assembled condition ready for use. The drug delivery device may be a disposable device. The term "disposable" means that the drug delivery device cannot be reused after an available amount of medication has been delivered from the drug delivery device. The drug delivery device may be configured to deliver a liquid medication. The medication may be, for example, insulin.

The term "medication", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

DETAILED DESCRIPTION

Figure 1:
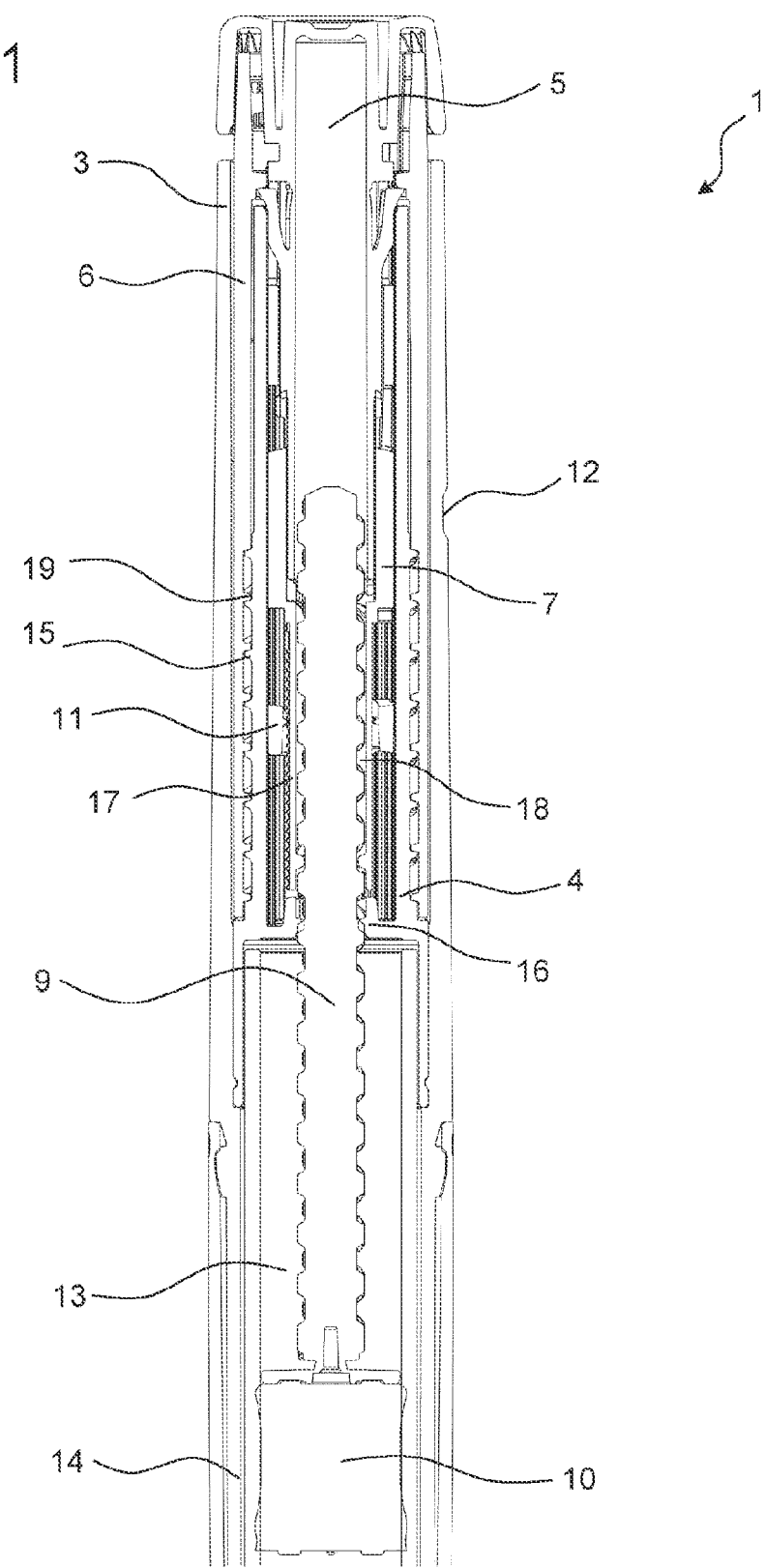
FIG. 1 shows a sectional view of a drug delivery device.

FIG. 1 shows a drug delivery device 1. In particular, the drug delivery device 1 is an injection device. The drug delivery device 1 is a variable dose device such that a user can select the size of a dose. The drug delivery device 1 is configured for multiple dose applications. The device can be delivered to a user in a fully assembled condition ready for use. The device has a low part count and is particularly attractive for cost-sensitive device applications.

The drug delivery device 1 comprises a housing 3, an inner body 4, an actuator 5, an indicator 6, a driver 7, a piston rod 9, a piston 10, a last dose stop 11, and a cartridge 13. A needle arrangement comprising a needle hub and a needle cover may be provided as additional components.

The housing 3 is a generally tubular element. A distal part of the housing 3 forms a cartridge holder 14 for receiving the cartridge 13.

The inner body 4 is a generally tubular element. The inner body 4 is received in the housing 3 and is permanently fixed therein to prevent any relative movement of the inner body 4 with respect to the housing 3. An external thread 15 is provided on the outer surface of the inner body 4. At its distal end, the inner body 4 comprises a further thread 16.

The actuator 5 is configured as a button. The actuator 5 is rotationally and axially moveable with respect to the housing 3 and the inner body 4. The actuator 5 is arranged at a proximal end of the drug delivery device 1. The actuator 5 is configured to be operated in order to dispense a dose of medication.

The indicator 6 is a generally tubular element. In particular, the indicator 6 is configured as a rotation member 43. In particular, the indicator 6 is configured to rotate with respect to the housing 3 during the setting and the dispensing of a dose. The indicator 6 is arranged concentrically around the inner body 4. In particular, the indicator 6 comprises an internal thread 19 engaging with the external thread 15 of the inner body 4. Thus, the indicator 6 is arranged between the inner body 4 and the housing 3. A series of numbers is provided, e.g. printed, on the outer surface of the indicator 6. The numbers are arranged on a helical line such that only one number or only a few numbers are visible through a window 12 of the housing 3. The numbers indicate the amount of a set dose. At the end of a dose dispense operation, the indicator 6 may have returned in its initial position, thereby indicating the end of a dispense operation to a user.

The piston rod 9 is configured as a lead screw. In particular, the piston rod 9 comprises two counter-handed threads which overlap each other. One of the threads of the piston rod 9 engages with the inner thread 16 of the inner body 4.

The driver 7 is a generally tubular element. An inner surface of the driver 7 has an inner thread 18 engaging with one of the external threads of the piston rod 9. The driver 7 is at least partly located within the inner body 4. A distal region of the driver 7 has an external thread 17. The driver 7 is configured to rotate and axially move with respect to the housing 3 during the setting of a dose. During the dispensing of a dose, the driver 7 is axially moveable and rotationally fixed with respect to the housing 3.

The last dose stop 11 is provided between the inner body 4 and the driver 7. An internal thread of the last dose stop 11 engages with the external thread 17 of the driver 7. The last dose stop 11 is configured to inhibit the setting of a dose which is larger than an amount of medication remaining in the cartridge 13. This is achieved by the last dose stop 11 abutting an abutment feature of the driver 7 when a dose is set which corresponds to an amount of medication remaining in the cartridge 13. The last dose stop 11 is configured as a nut.

In order to set a dose, the actuator 5 is rotated by a user. During the setting of a dose, the indicator 6 and the driver 7 are rotationally fixed with respect to the actuator 5. Thereby, the actuator 5, the indicator 6 and the driver 7 are rotated out of the housing 3. Thereby, the driver 7 is rotated along the piston rod 9 in a proximal direction, while the piston rod 9 is axially and rotationally fixed with respect to the housing 3 during the setting of a dose. The indicator 6 is rotated along the thread 15 of the inner body 4.

In order to dispense a dose, the actuator 5 is operated by a user. In particular, the actuator 5 is pushed in a direction towards a dispensing end of the device. During the dispensing of a dose, the actuator 5 and the driver 7 are rotationally fixed with respect to each other. The indicator 6 may rotate with respect to the actuator 5 and the driver 6 during the dispensing of a dose. Thereby, the indicator 6 may rotate back to its initial position and indicate the end of the dispense operation to a user. When the actuator 5 is operated, the driver 7 is also moved in a direction towards a dispensing end of the device. Thereby, the piston rod 9 is axially moved in a distal direction in order to dispense a dose of medication. In particular, the piston rod 9 is configured to rotate and axially move during the dispensing of a dose.

During a dispense operation, the piston 10 may be slightly deformed. This may occur due to a force of the piston rod 9 acting on the piston 10, and due to the pressure of the fluid in the medicament cartridge 13. When the actuator 5 has been operated and reached an end position, the piston 10 may relax to its undeformed shape, thereby pressing medication out of the medicament cartridge 13. Therefore, there may still be medication delivered from the drug delivery device 1 after the actuator 5 has reached its end position. The end position of the actuator 5 may be its most distal position. In particular, the actuator 5 is in its end position when it is fully depressed.

When the desired amount of a dose has been completely delivered, a feedback is given to a user. In particular, a feedback is given after a dwell period. The dwell period is the time between the moment when the actuator 5 has reached its end position and the moment when the full amount of a dose has been dispensed. In particular, the dwell period may be the time the piston 10 needs after an operation of the actuator 5 to relax to its undeformed state. Furthermore, the dwell period may be the time the tissue of a user needs to absorb the medication. By giving a feedback to the user at the end of the dwell period, it may be inhibited that a user releases the actuator 5 or withdraws the device from the skin before the full amount of a dose has been dispensed. Thereby, the dosing accuracy may be increased.

In FIGS. 2 to 16, different embodiments of a feedback feature 2 are shown, which may indicate that the full amount of medication has been delivered to a user. In particular, the feedback features 2 may indicate the end of a dwell period to a user. In particular, FIGS. 2 to 7 and 9 to 16 show different assemblies 60 for a drug delivery device 1 comprising different embodiments of a feedback feature 2. The embodiments are illustrated in the context of the drug delivery device 1 as shown in FIG. 1, but are not limited thereon. In particular, the feedback feature 2 may also be used in a reusable device or in a device having a different drive mechanism.

Figure 2:
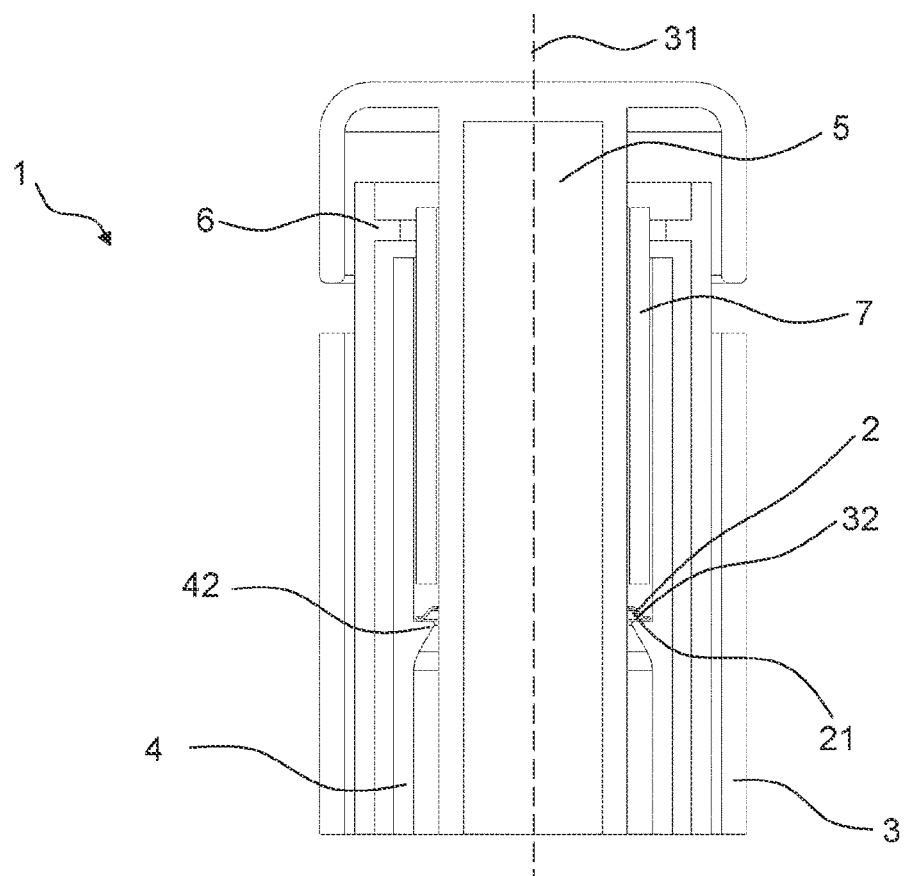
FIG. 2 shows a proximal part of a drug delivery device in a sectional view.

FIG. 2 shows a proximal part of a drug delivery device 1 comprising a feedback feature 2. The feedback feature 2 comprises a first feedback element 32 and a second feedback element 42. The first feedback element 32 is configured as a snap feature. In particular, the first feedback element 32 is configured as a resilient member 21. The first feedback element 32 may comprise an elastomeric material. In particular, the first feedback element 32 is configured as an elastomer washer. The first feedback element 32 is attached to the driver 7. In particular, the first feedback element 32 may be bonded or clipped to the driver 7. When the first feedback element 32 is in an undeformed condition, it comprises the shape of a dome.

When the driver 7 moves towards the distal end of the device during a dispense operation, the first feedback element 32 contacts a second feedback element 42. The second feedback feature 42 is located at the inner body 4. The second feedback element 42 is configured as a protrusion. In particular, the second feedback element 42 is configured as a full ring detent feature. This is beneficial in the case that the actuator 5 may have any rotational alignment relative to the inner body 4.

When the driver is further moved in a distal direction, the first feedback element 32 passes the second feedback element 42. Thereby, the first feedback element 32 is flipped inside out. Thereby, the first feedback element 32 is in a quasi-static state. When the driver 7 is in its most distal position after a dispense operation, the first feedback element 32 has lost contact with the second feedback element 42. Then, the first feedback element 32 is in a distal position relative to the second feedback element 42.

The material of the first feedback element 32 is chosen such that it reverts back to its undeformed shape after a well-defined period of time, in particular several seconds. In particular, this period depends on the internal hysteresis damping of the material. At a certain point, the first feedback element 32 snaps back to its undeformed state. This rapid motion generates an audible click and a vibration which can be felt by a user. Thereby, an audible and tactile signal is given to a user at the end of a dwell period.

During the setting of a dose, the first feedback feature 32 may be moved in a proximal direction together with the driver 7, such that after the setting of a dose, the first feedback feature 32 is again in a proximal position relative to the second feedback feature 42.

In an alternative embodiment, a further feature could be added to the inner body 4 or the driver 7, which may be impacted by the first feedback element 32 in order to produce a more distinct noise.

Figure 3:
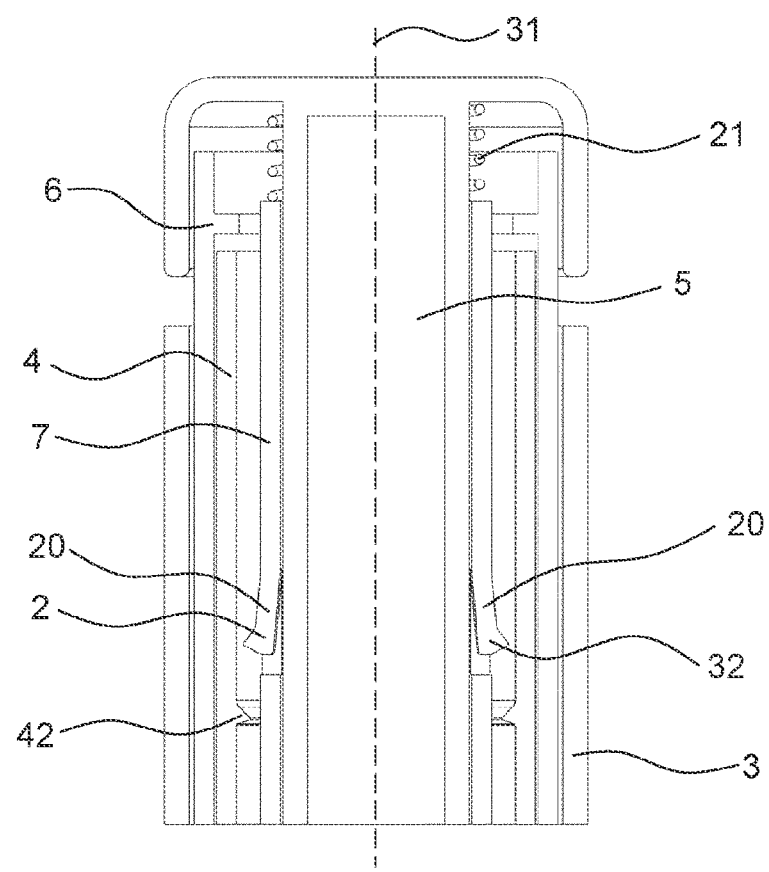
FIG. 3 shows a proximal part of a drug delivery device in a sectional view.

FIG. 3 shows a proximal part of a drug delivery device 1 comprising a further embodiment of a feedback feature 2.

The feedback feature 2 comprises a first feedback feature 32. The first feedback element 32 is integrally formed with the driver 7. In particular, the driver 7 may be an injection moulded part, wherein the first feedback element 32 may be integrally moulded with the driver 7. The first feedback element 32 comprises at least one, in particular two flexible arms 20, which stick out from the driver 7 in a radial direction. In particular, the flexible arms 20 stick out in a direction away from a longitudinal axis 31 of the drug delivery device 1. The flexible arms 20 may be configured as a snap feature. In particular, the flexible arms 20 are configured to snap over a second feedback element 42 of the feedback feature 2. The flexible arms 20 extend in a distal direction. In particular, each flexible arm 20 has one connection point with a main body of the driver 7 and one free end. The free end is faced towards a distal end of the device 1.

In this embodiment, a resilient member 21 is arranged between the actuator 5 and the driver 7. The resilient member 21 may be a spring, for example a coil spring. The resilient member 21 is compressed during the dispense of a dose. In particular, the resilient member 21 is compressed by the actuator 5 being moved in a distal direction. When the actuator 5 has reached its most distal position, the resilient member 21 is allowed to relax. The most distal position of the actuator 5 is a position which is closest to the dispensing end of the device. Thereby, the resilient member 21 drives the driver 7 in a distal direction. Thereby, the piston rod 9 continues to drive the piston 10 in a cartridge 13 towards a distal end of the device.

The force driving the driver 7 in a distal direction reduces with a direct relationship to its axial position. This is due to a relaxation of the resilient member 21. In particular, a force which is exerted on the driver 7 by the resilient member 21 reduces, since the tension force of the resilient 21 member reduces. The piston 10 may also relax as the compression force on it reduces.

When the driver 7 reaches a certain axial position, an audible and tactile feedback is created. This is achieved by the first feedback element 32 interacting with the second feedback element 42. The second feedback element 42 is configured as a protrusion at the inner body 4. In particular, the second feedback element 42 is configured as a full detent ring. This is because the driver 7 may have any rotational alignment relative to the inner body 4.

Figure 8A:
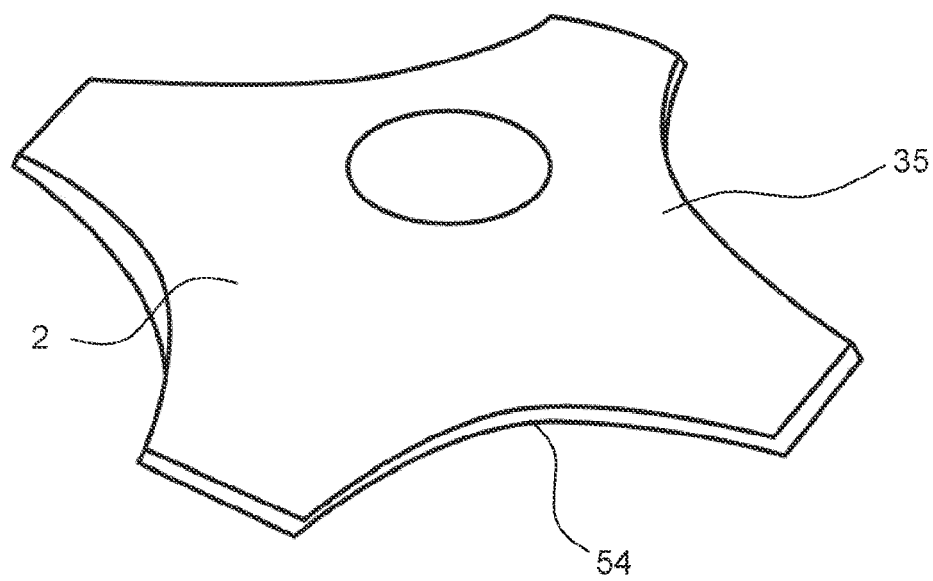
FIG. 8A shows a further embodiment of a feedback feature.
Figure 8B:
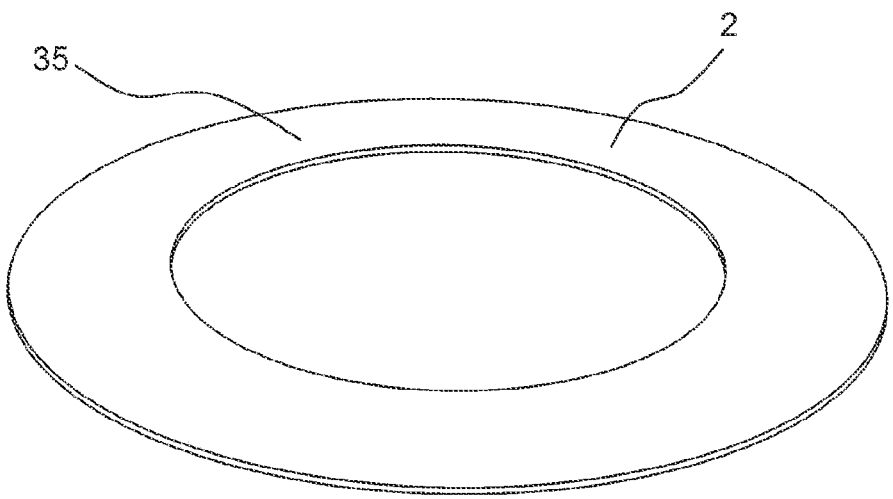
FIG. 8B shows a further embodiment of a feedback feature.

In an alternative embodiment, the flexible arms 20 may be arranged at the inner body 4, and the protrusion may be arranged at the driver 7. In an alternative embodiment, the signal could be provided by a snap feature, in particular a snap dome. The snap feature could be arranged between the driver 7 and the inner body 4. In particular, the snap feature could be supported by a protrusion in the inner body 4. A snap feature is shown in FIGS. 8A and 8B.

Figure 4:
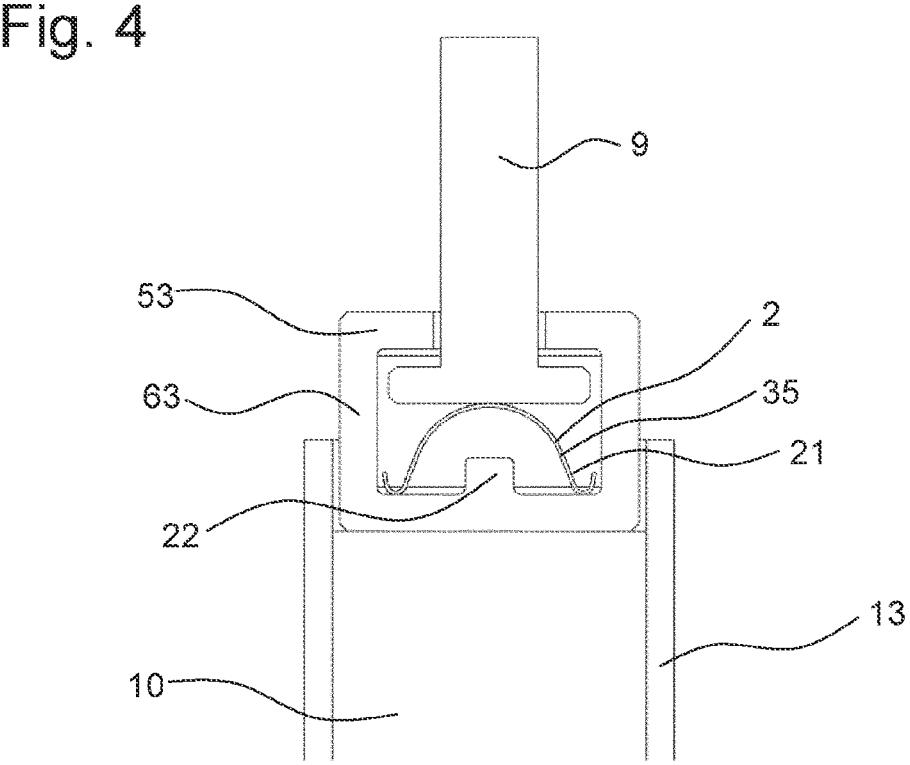
FIG. 4 shows an embodiment of a feedback feature.

FIG. 4 shows a different embodiment of a feedback feature 2. The feedback feature 2 comprises a resilient element 21. The resilient element 21 is configured as a snap feature 35. The snap feature 35 is configured as a snap dome. The snap feature 35 may comprise a metal material. The assembly comprises a piston rod 9. The feedback feature 2 is arranged at a distal end of the piston rod 9. Furthermore, an element 63 is arranged at a distal end of the piston rod 9. In particular, the piston rod 9 is partially arranged inside the element 63. The element 63 may be configured as a bearing 53. The element 63 may be at least partially located inside a cartridge 13. In particular, the element 63 may be configured to be moved inside the cartridge 13 by the piston rod 9. The feedback feature 2 is arranged inside the element 63. In particular, the element 63 is hollow. The element 63 is in contact with the piston 10. Thereby, a movement of the element 63 may cause a movement of the piston 10.

During a dispense operation, the piston rod 9 is moved in a distal direction. Thereby, the snap feature 35 is compressed by the piston rod 9. Thereby, the snap feature 35 may change to an unstable flattened state. In particular, the dispense force of the actuator 5 is transmitted to the piston 10 via the snap feature 35. When the actuator 5 has reached its end position, the snap feature 35 will be allowed to relax to its undeformed, stable state. Thereby, the snap feature 35 may continue to push the piston 10 in a distal direction into the cartridge 13. Since the compressive load on the piston 10 reduces, the piston 10 is also allowed to relax. When the compressive load on the snap feature 35 has reduced to a certain amount, the snap feature 35 snaps back to its original undeformed state. Thereby, an audible and tactile feedback may be given to a user. In particular, a feedback is given to a user when the compressive load on the piston 10 has reduced to a level that has allowed sufficient relaxation of the piston 10. In particular, a feedback is given at the end of a dwell period.

The snap action of the snap feature 35 may predominantly act in a radial direction, with only a small axial motion. Thereby, a damping of the snap action by a remaining axial load on the snap feature 35 may be prevented.

Furthermore, an impact feature 22 is provided, which is located in the bearing 53. In particular, the impact feature 22 is located at a distal face of the hollow interior of the bearing 53. The impact feature 22 may be configured for the snap feature 35 to impact in order to increase the audible and tactile feedback.

In an alternative embodiment, the feedback feature 2 may be located anywhere in the load path between the actuator 5 and the piston 10.

Figure 5:
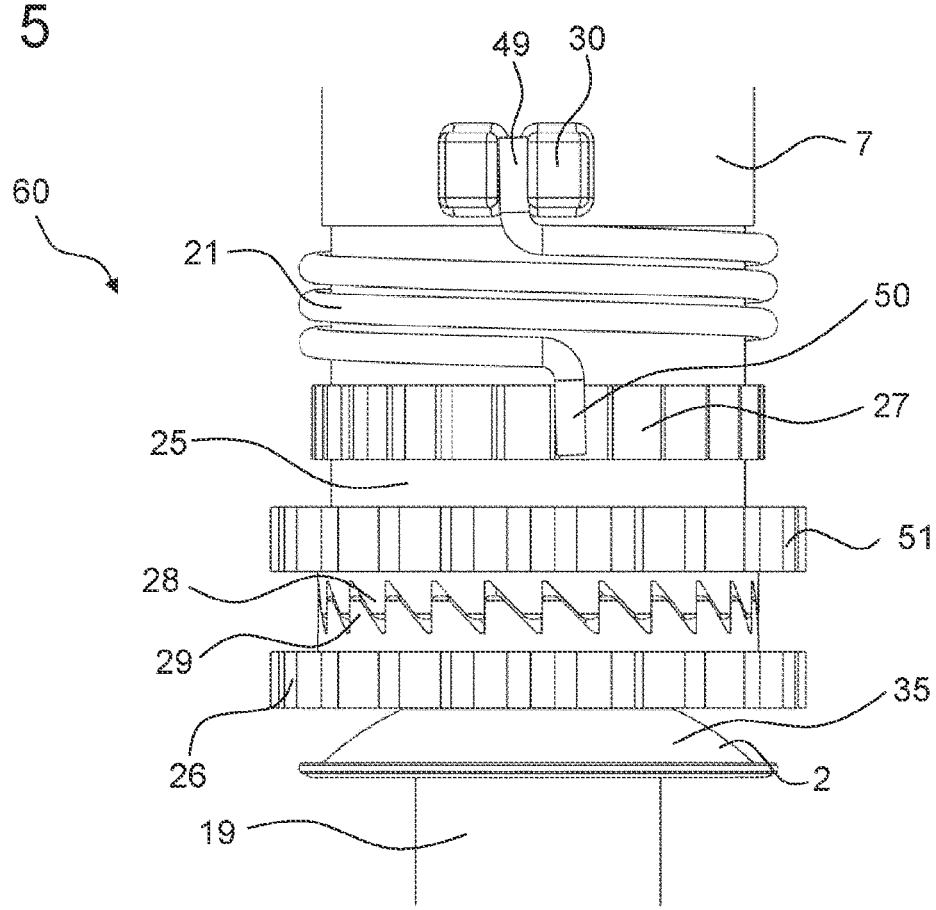
FIG. 5 shows an assembly for a drug delivery device.

FIG. 5 shows a further embodiment of an assembly 60 for a drug delivery device 1. The assembly 60 comprises a feedback feature 2. The feedback feature 2 is configured as a snap feature 35. The snap feature 35 is configured as a snap dome. Furthermore, the assembly comprises a sleeve member 25. The sleeve member 25 is attached to the driver 7. The assembly further comprises a resilient member 21. The resilient member 21 is configured as a torsion spring. The resilient member 21 comprises two free ends 49, 50. The first free end 49 is attached to the driver 7. In particular, the first free end 49 is fastened in a slot 30 of the driver 7. The second free end 50 of the resilient member 21 is attached to the sleeve member 25. The sleeve member 25 comprises a ratchet feature 27. The ratchet feature 27 comprises a plurality of steps or teeth, which are arranged circumferentially around the sleeve member 25. The second free end 50 of the resilient member 21 is engaged with the ratchet feature 27. In particular, the second free end 50 of the resilient member 21 rests between two steps of the ratchet feature 27. At a distal end of the sleeve member 25, an axially moveable member 26 is arranged. The axially moveable member 26 comprises a set of ramp features 29. The set of ramp features 29 of the axially moveable member 26 is engaged with another set of ramp features 28 of the sleeve member 25. The axially moveable member 26 is in contact with the snap feature 35. In particular, the axially moveable member 26 may interact with the snap feature 35 in order to create a feedback signal at the end of a dwell period. The snap feature 35 may be supported by a step in the inner body 4 (not shown).

During the setting of a dose, the sleeve member 25 is rotationally locked to the inner body 4 via spline features 51. Therefore, when the driver 7 rotates during the setting of a dose, the resilient member 21 is wound up. Since the second free end 50 of the resilient member 21 is engaged with the ratchet feature 27, the resilient member 21 is rotationally restrained.

Figure 6:
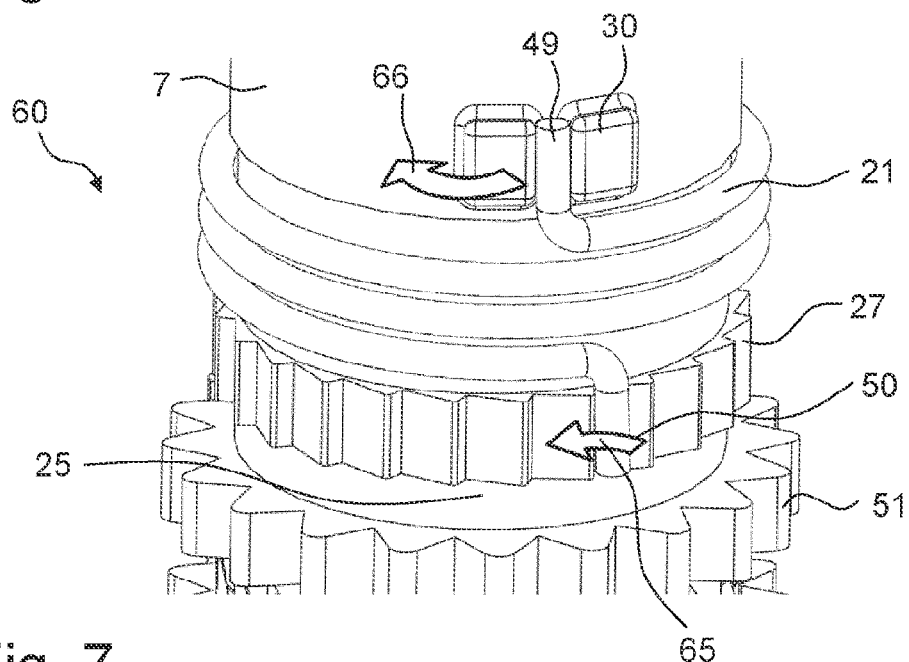
FIG. 6 shows parts of the assembly of FIG. 5 in a more detailed view.

FIG. 6 shows the engagement of the resilient member 21 with the driver 7 and the sleeve member 25 in a more detailed view. During the setting of a dose, the driver 7 is rotated with respect to the sleeve member 25 as indicated by arrow 66. When the driver 7 is rotated, the resilient member 21 is wound up. When the torque in the resilient member 21 reaches a certain value, the second free end 50 of the resilient member 21 is forced out of engagement of the ratchet feature 27. In particular, the resilient member 21 is forced to flex outwards by the ratchet feature 27. Thereby, the second free end 50 of the resilient member 21 may skip back in ratchet feature 27 by one step, as indicated by arrow 65. The torque, which is needed to temporarily disengage the resilient member 21 from the ratchet feature 27 is created by the setting of a dose of between one and two units. In particular, when a first unit is set, the driver 7 rotates and the resilient member 21 is wound up. Yet, the resilient member 21 does not disengage from the ratchet feature 27, such that one unit's rotation is wound into the resilient member 21. If a user continues to set a dose to a second unit or above, the torque in the resilient member 21 will rise further and cause the second free end 50 to slip backwards to a previous step of the ratchet feature 27. Therefore, regardless of how many units are set, the resilient member 21 will always be wound up by the same amount.

Figure 7:
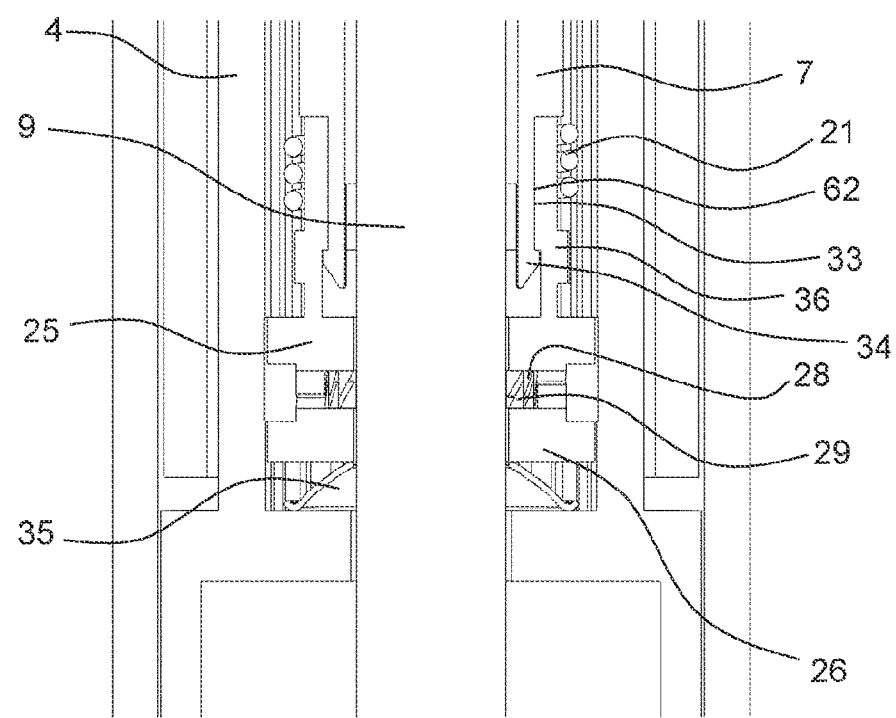
FIG. 7 shows the assembly of FIG. 5 in a sectional view.

At the end of the dispense operation, the sleeve member 25 moves in a distal direction out of the engagement with the inner body 4. This is due to the sleeve member 25 being axially coupled to the driver 7, as shown in FIG. 7. At this point, the torque which is wound into the resilient member 21 will cause the sleeve member 25 to rotate.

The axially moveable member 26, which is shown in FIGS. 5 and 7, is rotationally locked to the inner body 4. This is achieved by a series of spline features. As the sleeve member 25 rotates, the axially moveable member 26 is pushed in a distal direction. In particular, due to the rotation of the sleeve member 25, the ramp features 29 of the axially moveable member 26 are forced out of engagement with the ramp features 28 of the sleeve member 25. When the axially moveable member 26 moves in a distal direction, it compresses the snap feature 35. Thereby, the snap feature 35 is caused to snap through and produce an audible and/or tactile signal to the user.

As the resilient member 21 is always wound up by the same amount, regardless of the number of units set, the torque acting on the sleeve member 25 will always be the same and the dwell period will also be constant.

FIG. 7 shows the assembly of FIG. 6 in a sectional view. The sleeve member 25 is clipped to the driver 7. In particular, the driver 7 comprises engagement features 34, which engage with a corresponding engagement feature 36 of the sleeve member 25. Thereby, the sleeve member 25 is axially fixed to the driver 7. The sleeve member 25 can rotate relative to the driver 7. At an interface 33 between the driver 7 and the sleeve member 25, a damping feature 62 is provided. The damping feature 62 comprises a thin layer of viscous fluid. Thereby, sheer stress is generated during a relative rotation of the driver 7 with respect to the sleeve member 25, which provides damping. In particular, the rotation of the sleeve member 25 is retarded by the damping. Thereby, the relaxation of the resilient member 21 during a dwell period is retarded. By controlling the ratio of damping relative to the stiffness of the resilient member 21, the delay between the end of movement of the actuator 5 and the feedback signal can be set to the desired dwell period. During the setting of a dose, the damping may increase the perceived quality of the drug delivery device.

FIG. 8A shows a feedback feature 2 being configured as a snap feature 35. The snap feature 35 is configured as a snap dome. In particular, the feedback feature 2 is configured as an arched disc. Furthermore, the feedback feature 2 comprises at least one recess 54. The recess 54 is configured as a concave cavity. In particular, the first feedback element 32 comprises four recesses 54. Due to the recesses 54, the snap feature 35 comprises a sufficient flexibility. The feedback feature 2 is configured to snap through when it is compressed above a certain load. Thereby, the feedback feature 2 creates an audible click and/or a tactile feedback at the end of a dispense operation.

In an alternative embodiment as shown in FIG. 8B, the snap feature 35 is configured without any recess. Thereby, the snap feature 35 may comprise a high stiffness. Thereby, the feedback signal may be more distinct. In particular, the snap feature 35 is configured as an arched ring. In particular, the snap feature 35 comprises an opening.

Figure 9:
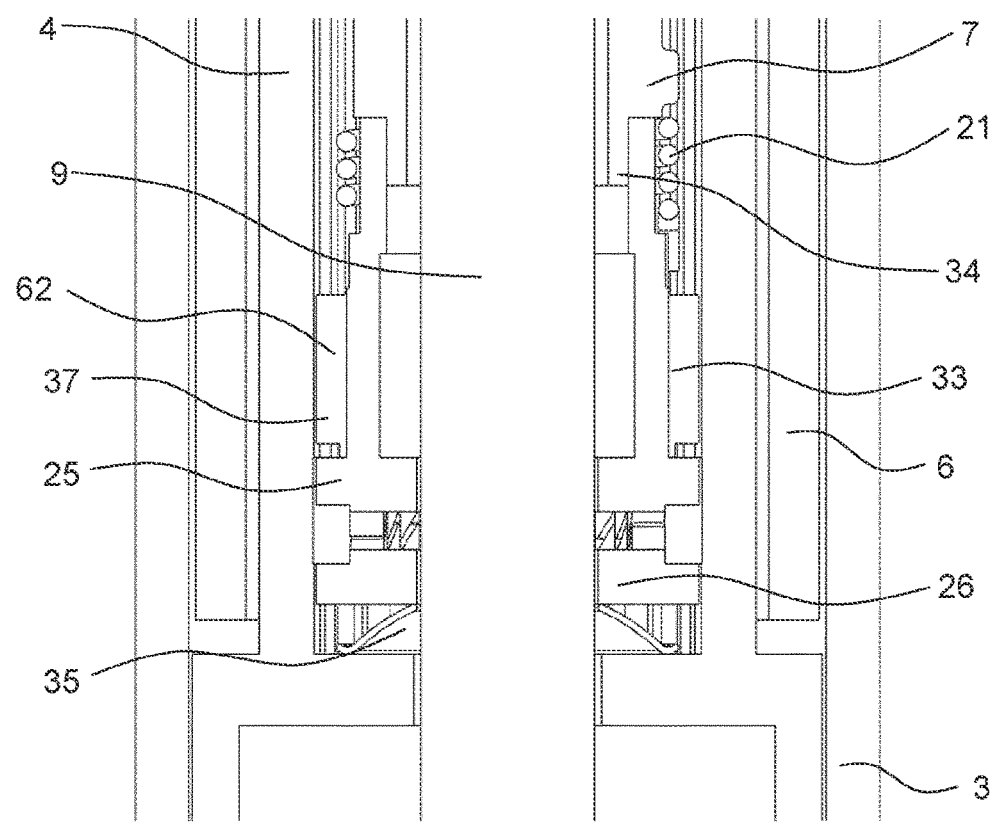
FIG. 9 shows a sectional view of a further embodiment of a drug delivery device.

FIG. 9 shows a further assembly 60 for a drug delivery device 1 comprising a feedback feature 2 in a sectional view. The embodiment is similar to the embodiment shown in FIGS. 5 to 7. In the embodiment shown in FIG. 9, the damping feature 62 comprises a damper sleeve 37. The damper sleeve 37 is splined to the inner body 4 and rotationally fixed with respect to the inner body 4. The damper sleeve 37 is free to translate axially with the sleeve member 25. The damping interface 33 is now between the sleeve member 25 and the damper sleeve 37. The interface between the driver 7 and the sleeve member 25 is changed to a free running bearing fit. The operation of the mechanism is otherwise unchanged. One benefit of this embodiment is that there is damping acting on the actuator 5 during a setting of a dose. Furthermore, the sleeve member 25 and the damper sleeve 37 could be manufactured and assembled as a subassembly, for example by an existing rotary damper supplier.

Figure 10:
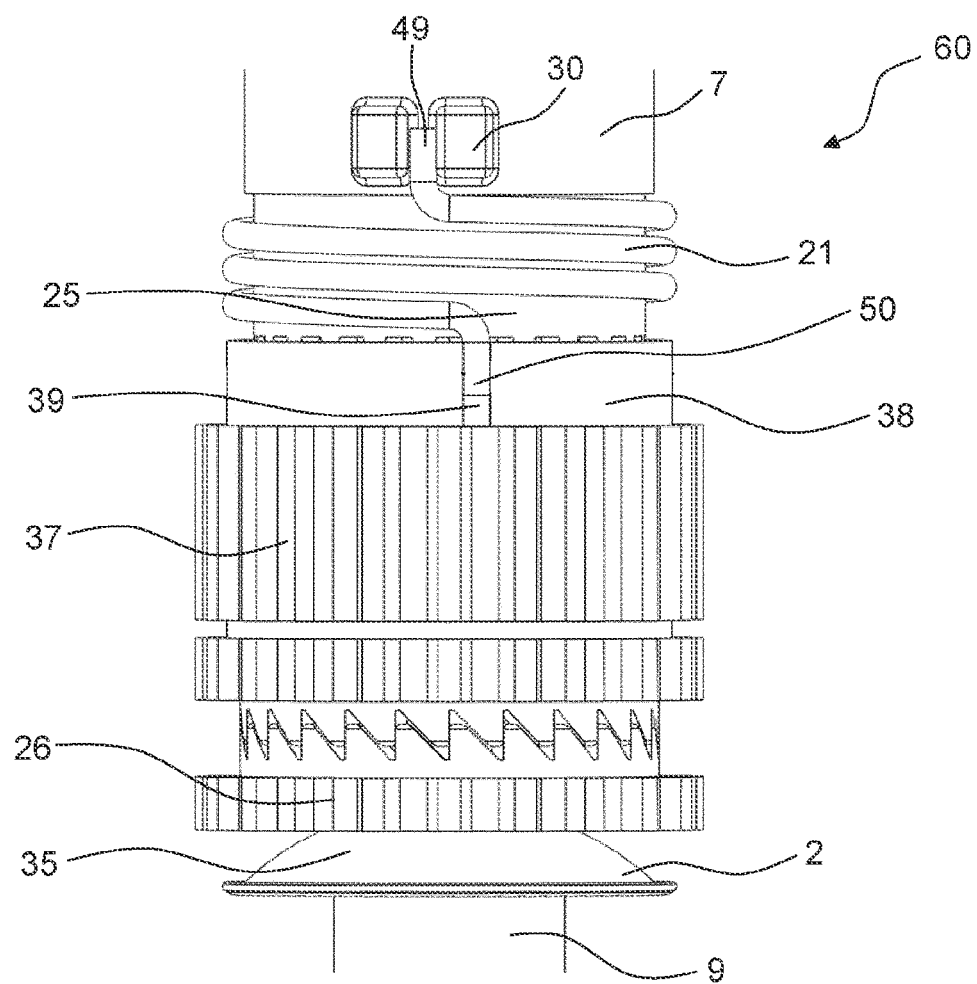
FIG. 10 shows a further assembly for a drug delivery device.

FIG. 10 shows a further assembly 60 for a drug delivery device comprising a feedback feature 2. This embodiment is similar to the embodiment shown in FIG. 9, besides that a clutch member 38 is added to the assembly. The second free end 50 of the resilient member 21 is attached to the clutch member 38. The clutch member 38 is engaged with the sleeve member 25, in particular with a ratchet feature 27 (see FIG. 11). The ratchet feature 27 is arranged at the sleeve member 25. The clutch member 38 is configured to stay locked relative to the sleeve member 25 as the first unit is set. When a second unit is set, the clutch member 38 is temporarily disengaged from the ratchet feature 27 and begins to slip relative to the sleeve member 25. Thereby, the resilient member 21 is only wound up during the setting of a first unit. In the shown embodiment, the resilient member 21 does not directly interact with the ratchet feature 27. The function of the mechanism is otherwise unchanged.

Figure 11:
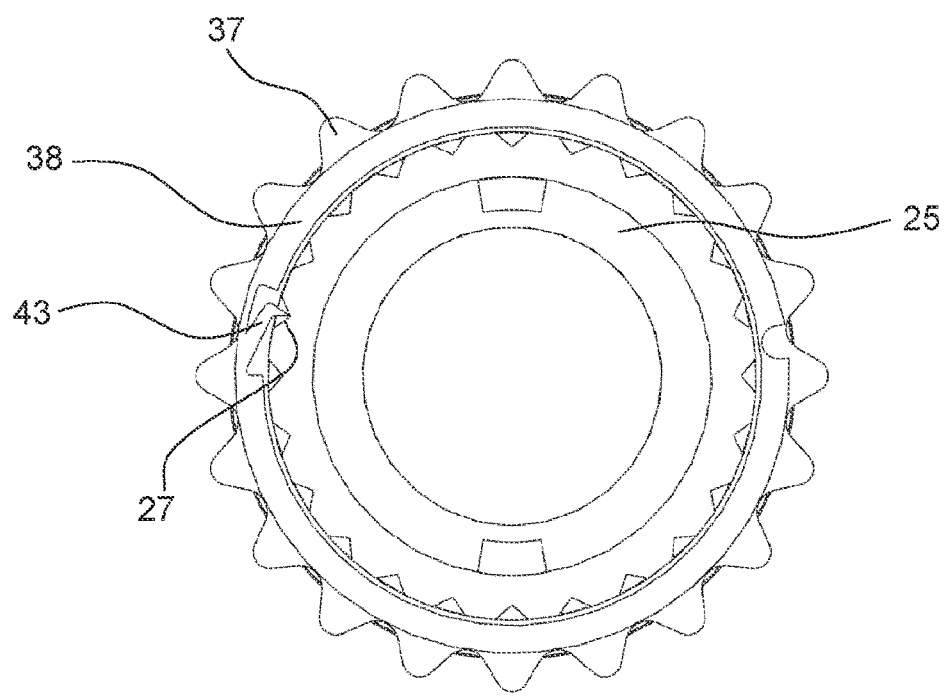
FIG. 11 shows a section through the assembly of FIG. 10.

FIG. 11 shows a sectional view of the sleeve member 25, the clutch member 38 and the damper sleeve 37. The clutch member 38 comprises a ratchet arm 43 which is engaged with the ratchet feature 27. Via the ratchet arm 43, the clutch member 38 is configured to transmit a certain maximum amount of torque to the sleeve member 25. In particular, the clutch member 38 will transmit a torque to the sleeve member 25 via the ratchet arm 43. Thereby, the sleeve member 25 may be rotated during a dwell period.

Figure 12:
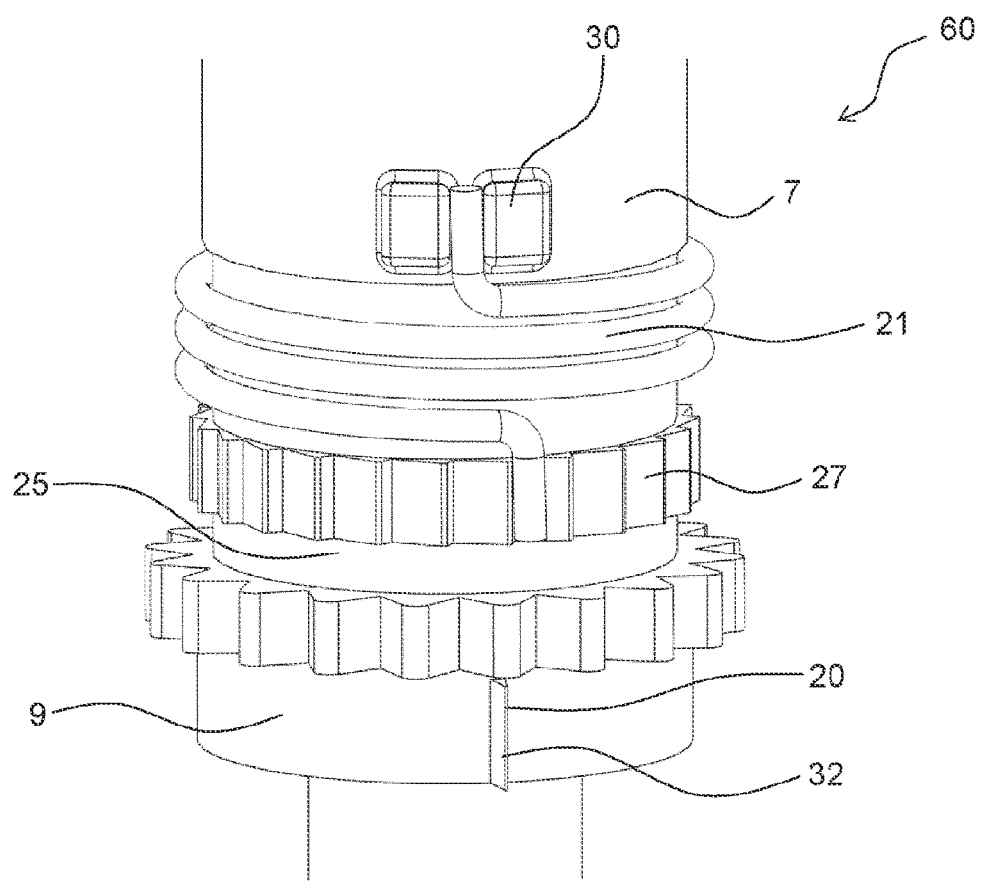
FIG. 12 shows a further assembly for a drug delivery device.

FIG. 12 shows a further embodiment of an assembly 60 for a drug delivery device 1. This embodiment is similar to the embodiment shown in FIGS. 5 to 7. Instead of the axially moveable member 26 and the snap feature 35, the assembly comprises a flexible arm 20. The flexible arm 20 acts as a first feedback element 32. The flexible arm 20 is attached to the sleeve member 25.

Figure 13:
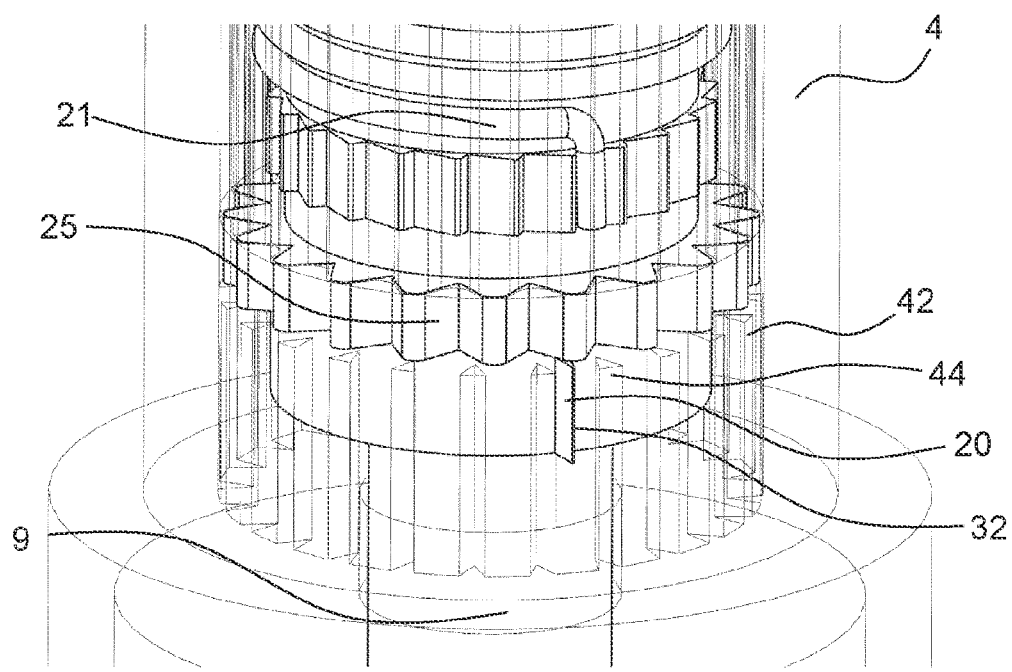
FIG. 13 shows the assembly of FIG. 12 arranged in an inner body of a drug delivery device in a partially transparent view.

FIG. 13 shows the assembly 60 arranged in the interior of the inner body 4. The inner body 4 is shown transparent for a better understanding of the mechanism. The inner body 4 comprises a second feedback element 42. The second feedback element 42 comprises splines 44 which are configured to interact with the first feedback element 32, in particular with the flexible arm 20. The splines 44 are arranged circumferentially at an inner surface of the inner body 4.

When the actuator 5 has reached its end position, the sleeve member 25 is rotated by the torque of the resilient member 21, as already described with reference to the previous embodiments. Thereby, the flexible arm 20 is moved along the spline features 44 of the inner body 4. For example, the flexible arm 20 may interact with one spline 44 of the inner body 4 at the end of a dwell period, thereby producing an audible click. The embodiment shown in FIG. 13 could also be combined with the embodiments shown in FIGS. 5, 9 and 7.

Figure 14:
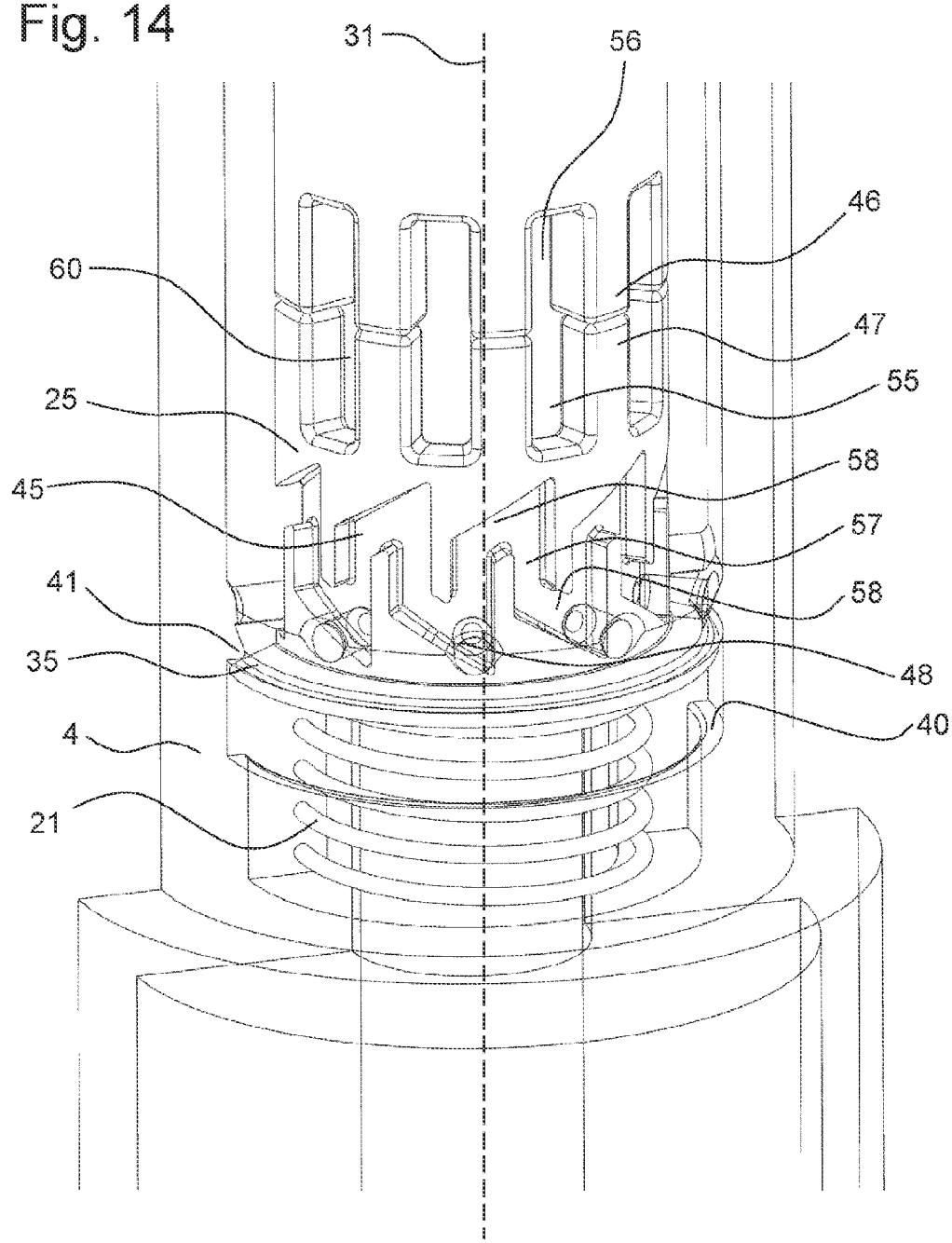
FIG. 14 shows a further assembly for a drug delivery device arranged in an inner body of a drug delivery device in a partially transparent view.

FIG. 14 shows a schematic view of a further embodiment of a drug delivery device 1 comprising a feedback feature 2. In particular, FIG. 14 shows an assembly 60 arranged in an inner body 4. The inner body 4 is shown transparent for a better understanding of the mechanism. The feedback feature 2 is configured as a snap feature 35. The snap feature 35 is configured to interact with a first ridge 40 and a second ridge 41 of the inner body 4.

The assembly further comprises a sleeve member 25. The sleeve member 25 is axially moveable and rotatable with respect to the inner body 4. The snap feature 35 is attached to the sleeve member 25. In particular, the snap feature 35 is attached to a distal end of the sleeve member 25. Between the distal end of the sleeve member 25 and the inner body 4, a resilient member 21 is arranged. The resilient member 21 may be a spring, for example a coil spring. At a proximal end of the sleeve member 25 a set of castellations 47 is arranged. Between the castellations 47, the sleeve member 25 comprises recesses 55. The driver 7 comprises a further set of castellations 46 at its distal end. Between the castellations 46, the driver 7 comprises recesses 56.

The sleeve member further comprises a groove 45. The groove 45 comprises straight groove sections 57, which extend along a longitudinal axis 31 of the device 1. Furthermore, the groove 45 comprises diagonal groove sections 58, which are inclined with respect to a longitudinal axis 31 of the device. The groove 45 interacts with protrusions 48 of the inner body 4. The axial movement of the sleeve member 25 is limited by the interaction of the groove 45 with the protrusions 48 of the inner body 4.

When the driver 7 approaches its end position during the dispensing of a dose, the castellations 46 of the driver 7 abut the castellations 47 of the sleeve member 25. As the driver 7 is further moved in a distal direction, the sleeve member 25 is moved towards a distal end of the device by the driver 7. In this state, the protrusions 48 of the inner body 4 run in the straight sections 57 of the groove 45. In particular, the sleeve member 25 performs an axial, non-rotational movement. As the sleeve member 25 is moved towards a distal end of the device, the resilient member 21 is compressed. Furthermore, the snap feature 35 abuts the first ridge 40 of the inner body 4. Thereby, the snap feature 35 is caused to snap through, thereby producing an audible click. In particular, the audible click is produced when the driver 7, respectively the actuator 5 (not shown) is in its end position. In particular, a feedback is given to a user at the beginning of a dwell period.

When the driver 7 reaches its end position, the protrusions 48 of the inner body 4 interact with the diagonal groove sections 58 of the sleeve member 25. Thereby, the sleeve member 25 is rotated relative to the driver 7. Due to the rotation of the sleeve member 25, the castellations 47 of the sleeve member 25 engage with the recesses 56 of the driver 7 and vice versa. Therefore, the sleeve member 25 is now free to axially move in a proximal direction. The resilient member 21 is now enabled to relax. In particular, a movement of the sleeve member 25 in a proximal direction is caused by the resilient member 21. As the sleeve member 25 moves in a proximal direction, the snap feature 35 contacts the second ridge 41 of the inner body 4. Thereby, the snap feature 35 is caused to snap back to its previous form, thereby producing an audible feedback. In particular, this feedback indicates the end of a dwell period.

When a user releases the actuator 5, the sleeve member 25 is able to move further axially and the protrusions 48 of the inner body 4 interact with the groove 45 such that the sleeve member 25 is caused to rotate again. Thereby, the castellations 47, 46 are re-aligned, such that the device is ready for the next dispense.

Figure 15:
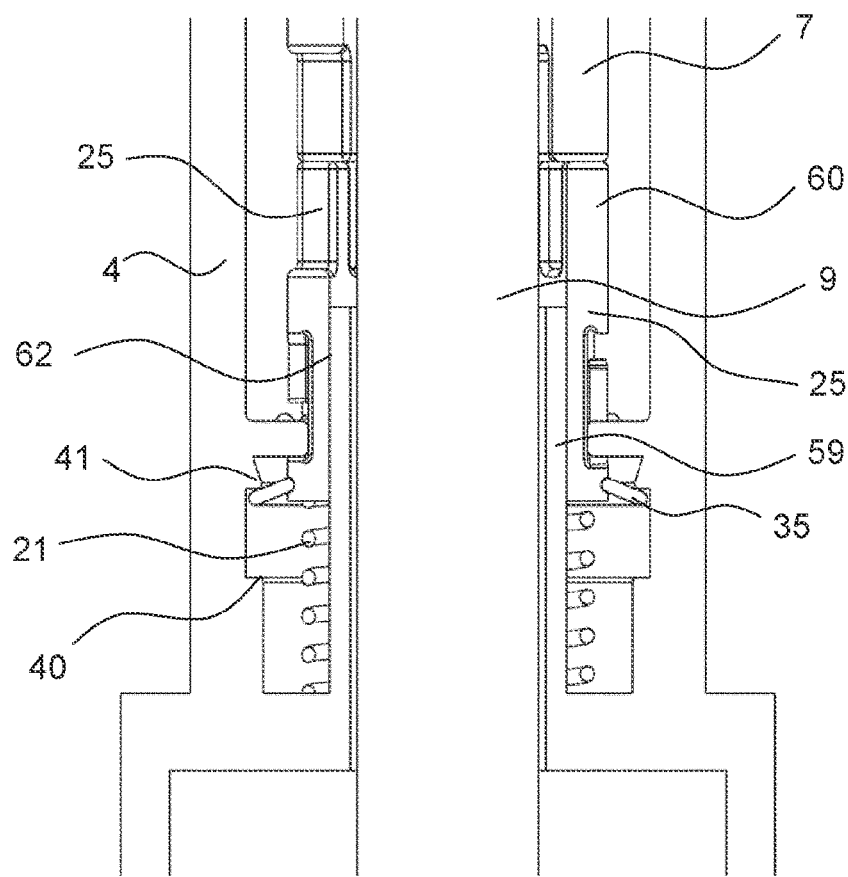
FIG. 15 shows the assembly of FIG. 14 in a sectional view.

FIG. 15 shows a sectional view of the embodiment shown in FIG. 14. At an interface 59 between the sleeve member 25 and the inner body 4, a damping feature 62 is provided. In particular, a thin layer of viscous fluid is provided at the interface 59. Thereby, the relaxation of the resilient member 21 may be impeded. Thereby, the feedback signal at the end of a dwell period may be delayed.

Figure 16:
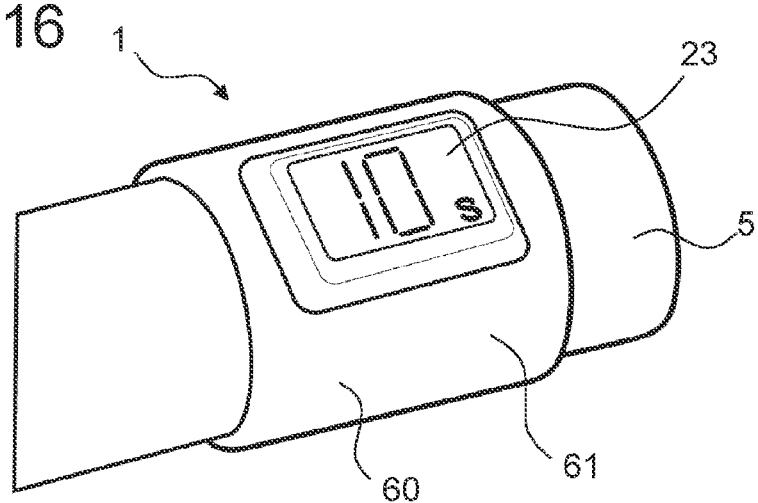
FIG. 16 shows a further embodiment of a feedback feature located at the proximal part of a drug delivery device.

FIG. 16 shows the proximal part of a further embodiment of a drug delivery device 1 and an assembly 60 for a drug delivery device. The drug delivery device 1 comprises an electronic module 61. The electronic module 61 may track the motion of the components of the drug delivery device 1. Thereby, the electronic module 61 may determine when a dispense operation is completed. The electronic module 61 may give a feedback to a user at the end of a dwell period. Additionally, a feedback may also be provided at the start of the dwell period. In particular, the electronic module 61 may comprise a visual display screen 23, a speaker, a tactile response, e. g. vibration, or any combination of these signalling methods.

The electronic module 61 comprises a timer which may be activated when the actuator 5 has reached its end position, in particular at the beginning of a dwell period. The remaining time of a dwell period may be shown on the display screen 23.

The display screen 23 may have additional functions, such as displaying the current dose during the setting of a dose. The display screen 23, the speaker and an associated circuitry could be incorporated into the drug delivery device 1 or clipped onto the drug delivery device as an optional accessory which could be retained by a user when disposing the drug delivery device 1.

The invention claimed is:

1. An assembly for a drug delivery device, the assembly comprising:
   a piston rod axially movable in a distal direction in order to dispense a dose of medication;

a driver, the driver being a generally tubular element, wherein an inner thread of the driver is engaged with an external thread of the piston rod;

an actuator coupled to the driver, the actuator configured to be operated directly by a user in order to dispense the dose of medication; and a feedback feature configured to give a feedback signal to the user at an end of a dwell period after the actuator has reached an end position and when the actuator is kept fully depressed in the end position.

2. The assembly according to claim 1, comprising a resilient member, wherein the resilient member is deformed during setting and/or dispensing of the dose, and wherein the feedback signal occurs after a relaxation of the resilient member.

3. The assembly according to claim 2, wherein the resilient member is configured as a spring member.

4. The assembly according to claim 2, wherein the relaxation of the resilient member causes the feedback signal to be given by the feedback feature.

5. The assembly according to claim 2, wherein the feedback feature comprises the resilient member, and wherein the feedback signal is given by the resilient member.

6. The assembly according to claim 2, comprising a ratchet feature, wherein the resilient member is coupled to the ratchet feature.

7. The assembly according to claim 6, wherein the resilient member is configured to be decoupled from the ratchet feature when a load on the resilient member exceeds a certain value.

8. The assembly according to claim 6, comprising a clutch member which is coupled to the ratchet feature, and wherein the clutch member is configured to be decoupled from the ratchet feature when a load on the resilient member exceeds a certain value.

9. The assembly according to claim 8, wherein the load on the resilient member is less than the certain value throughout the setting of the dose.

10. The assembly according to claim 2, comprising a damping feature, wherein the damping feature is configured to retard a relaxation of the resilient member.

11. The assembly according to claim 1, wherein the feedback feature comprises a snap feature, wherein the snap feature is configured to snap through at the end of the dwell period.

12. The assembly according to claim 1, wherein the feedback feature is configured to axially move during the dwell period.

13. The assembly according to claim 1, wherein the feedback feature comprises at least one flexible arm.

14. The assembly according to claim 1, wherein the feedback feature comprises a first feedback element and a second feedback element, the first feedback element being configured to rotate with respect to the second feedback element.

15. The assembly according to claim 1, wherein the feedback feature is arranged at a distal end of the piston rod.

16. The assembly according to claim 1, comprising an electronic module which is configured to track motion of components of the assembly in order to determine when the actuator is at an end position.

17. The assembly according to claim 1, wherein the end position is a most distal position of the actuator.

18. An assembly for a drug delivery device, the assembly comprising:

a piston rod axially movable in a distal direction in order to dispense a dose of medication;

a driver, the driver being a generally tubular element, wherein an inner thread of the driver is engaged with an external thread of the piston rod;

an actuator coupled to the driver, the actuator configured to be directly operated by a user in order to dispense the dose of medication; and a feedback feature being configured to give a feedback signal to the user at an end of a dwell period after the actuator has reached an end position, wherein the feedback signal is an audible and/or a tactile signal.

19. The assembly according to claim 18, comprising a resilient member, wherein the resilient member is deformed during setting and/or dispensing of the dose, and wherein the feedback signal occurs after a relaxation of the resilient member.

20. The assembly according to claim 19, wherein the resilient member is configured as a spring member.

* * * * *

UNITED STATES PATENT AND TRADEMARK OFFICE
CERTIFICATE OF CORRECTION

PATENT NO.       : 10,449,301 B2
APPLICATION NO.  : 14/770845
DATED            : October 22, 2019
INVENTOR(S)      : David Aubrey Plumptre et al.

It is certified that error appears in the above-identified patent and that said Letters Patent is hereby corrected as shown below:

In the Claims

Column 19, Line 40, Claim 9, before "setting", delete "the"

Signed and Sealed this
Thirty-first Day of December, 2019

Andrei Iancu
*Director of the United States Patent and Trademark Office*